United States Patent [19]
Shiba et al.

[11] 3,961,963
[45] June 8, 1976

[54] MULTILAYER PHOTOGRAPHIC MATERIAL

[75] Inventors: Keisuke Shiba; Takeshi Hirose; Toshiaki Aono, all of Minami-ashigara, Japan

[73] Assignee: Fuji Photo Film Co., Ltd., Minami-ashigara, Japan

[22] Filed: Sept. 13, 1974

[21] Appl. No.: 505,816

[30] Foreign Application Priority Data
Sept. 13, 1973  Japan.............................. 48-103542

[52] U.S. Cl............................. 96/100; 96/56; 96/67; 96/95
[51] Int. Cl.² ............................................. G03C 1/40
[58] Field of Search ................... 96/56, 95, 100, 67

[56] References Cited
UNITED STATES PATENTS

| | | |
|---|---|---|
| 3,379,529 | 4/1968 | Porter et al.............................. 96/36 |
| 3,536,487 | 10/1970 | Graham .................................. 96/59 |
| 3,617,291 | 11/1971 | Saudey................................... 96/100 |
| 3,622,328 | 11/1971 | Pollet et al............................. 96/100 |
| 3,756,821 | 9/1973 | Hayashi et al. ......................... 96/95 |

*Primary Examiner*—Edward G. Whitby
*Attorney, Agent, or Firm*—Sughrue, Rothwell, Mion, Zinn & Macpeak

[57] ABSTRACT

A photographic material comprising a support having thereon a photosensitive silver halide emulsion layer containing a hydroquinone derivative which releases a development inhibitor or a development accelerator at development and including an absorbing colloid layer for adsorbing the development inhibitor or accelerator containing silver halide particles which are not substantially developed by development on the silver halide emulsion layer or between the silver halide emulsion layer and the support.

13 Claims, 7 Drawing Figures

MULTILAYER PHOTOGRAPHIC MATERIAL

BACKGROUND OF THE INVENTION

1. Field of the Invention

The present invention relates to multilayer photographic photosensitive materials whereby image quality such as sharpness, graininess, exposure tolerance or color reproduction, etc. is improved and uniformity of finished quality at development is improved. Particularly, it relates to photographic photosensitive materials which do not exhibit development mottle or which do not result in an uneven finish on high temperature development.

2. Description of the Prior Art

It is known to use hydroquinone derivatives which release a development inhibitor at development in order to improve the image quality. For example, they are described in U.S. Pat. 3,379,529 as the so-called "IRD-Inhibitor Releasing Developers" or in U.S. Pat. No. 3,620,746, and Japanese Patent Applications 41870/1973 and 87723/1973 as the so-called "DIR-Hydroquinone-Development Inhibitor Releasing Hydroquinones". Hydroquinone derivatives which release a development accelerator at development have been used in order to provide a hard tone image or to accelerate image development. Further, they are used together with the so-called "DIR-compounds" such as "DIR-couplers" or "DIR-hydroquinones" in order to obtain excellent image quality.

In general, color photographic photosensitive materials comprise a blue sensitive emulsion layer containing a yellow coupler (BL), a green sensitive emulsion layer containing a magenta coupler (GL), a red sensitive emulsion layer containing a cyan coupler (RL), middle layers (ML), a filter layer which absorbs ultraviolet light or visual light of a specific wavelength (FL), an antihalation layer (AHL), a protective layer (PL) and a photosensitive emulsion layer prepared by varying the coupler and distribution of spectral sensitivity depending on the purpose, etc.

Particularly, in color photographic sensitive materials, many methods have been developed in order to improve color image quality, for example, color reproduction, color saturation, graininess of the color image and color sharpness, etc. For example, methods are described in Japanese Patent Application 33238/1973, 41870/1973 and 50051/1973, etc. "Interlayer Color Correction Hydroquinone Derivatives" defined in Japanese Patent Application 87723/1973 are used.

However, when these methods are practiced, serious defects appear.

A first defect is as follows. Namely, the development inhibitor or accelerator which was released at development diffuses into an adjacent layer to cause an interlayer interimage effect or undercut interimage effect, however that contaminates the developer by exudation and changes its developing ability. Consequently, the final finished quality at development is not uniform.

A second defect is that a compound which was released at development diffuses into an adjacent layer, is absorbed into the developer and partially inhibits neighboring development to cause development mottle. It is also known that iodine ions released at development exhibit an interlayer inter image effect and that the iodine ions are completely trapped by adjacent silver halide particles. It is also known that iodine ions cause an exchange reaction with silver bromide or silver chloride for red development. A third defect is that development mottle caused by "DIR-hydroquinone derivatives" is easily formed using a rapid developing treatment at a temperature higher than 30°C.

SUMMARY OF THE INVENTION

An object of the present invention is to improve these above-described defects.

This object can be attained with a photographic photosensitive material comprising a support having thereon a photosensitive silver handle emulsion layer containing a hydroquinone derivative which releases a development inhibitor or accelerator at development and having an adsorbing colloid layer for adsorbing the development inhibitor or accelerator containing silver halide which is not substantially developed at development on the emulsion layer or between the emulsion layer and the support.

DETAILED DESCRIPTION OF THE INVENTION

Figure 1:
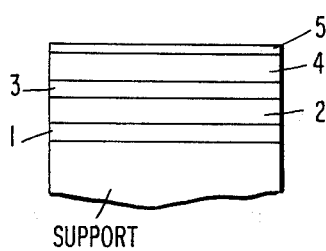
FIGS. 1, 2, and 3 show layer structures of samples used in the Examples.

According to preferred embodiments of the present invention, the multilayer color photosensitive material comprises at least two photosensitive emulsion layers which form images having different colors from each other by color development on a support, wherein at least one of the photosensitive emulsion layers contains the so-called "DIR-hydroquinone derivative" or "ICC-hydroquinone derivative", and an adsorbing colloid layer containing silver halide particles which adsorbs the organic development inhibitor released at development is positioned on the emulsion layer or between the emulsion layer and the support. Further, the photosensitive material of the invention can be a black-white photosensitive material which contains at least one photosensitive layer. This black-white photosensitive layer preferably contains the so-called "DIR-hydroquinone derivative".

The "DIR-development inhibitor releasing hydroquinone derivative" or the "interlayer color correction (ICC) hydroquinone derivative" means a compound which imagewise releases a diffusible development inhibitor at development and partially inhibits color development of adjacent photosensitive emulsion layer, whereby an interlayer color correction effect is obtained.

Preferred compounds are hydroquinone derivatives having a heterocyclic monothio group which can become a development inhibitor and an aliphatic thio group or aliphatic oxy group having 8 or more carbon atoms which functions as a diffusion resisting ballast group or precursors of such hydroquinone derivatives. Preferred compounds are represented by the following formula (I)

Formula (I)

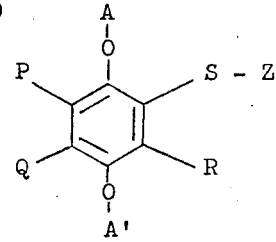

In the formula, A and A' each represents a hydrogen atom or a group which is released by alkali (e.g., an alkoxycarbonyl group or an acyl group) wherein A' may form a ring together with R or Q (e.g., an oxathiazole ring, etc.). P, Q and R each represents a hydrogen atom, an alkyl group (e.g., having 1 to 20 carbon atoms such as methyl, ethyl, 1,1,3,3-tetramethylbutyl and n-pentadecyl groups, etc.), an aryl group (e.g., phenyl and p-tolyl groups, etc.), an -S-Y residue (wherein Y represents an alkyl group, e.g., having 1 to 20 carbon atoms such as a 2-ethylhexyl, n-dodecyl, n-hexadecyl, or n-octadecyl group, a hydroxycarbonylmethyl group, an ethoxycarbonylmethyl group, a 2-hydroxyethyl group, or an aryl group such as phenyl group or a tolyl group, etc.), a hydroxyl group, a halogen atom such as chlorine, bromine, idoine and flourine, a -S-Z residue, an alkoxy group, e.g., having 1 to 20 carbon atoms in the alkyl moiety thereof, an aryloxy group (e.g., a methoxy group, an ethoxy group or an -O-Y residue, etc). or a heterocyclic ring, e.g., a 5-membered nitrogen containing heterocyclic ring such as pyridyl, benzotriaolyl,hydantionyl, etc. Z represents a heterocyclic residue which is substantially photographically inert in a bonded state and particularly Z represents a tetrazolyl group (e.g., a 1-phenyltetrazolyl group, etc.), a triazolyl group (e.g., a 4-phenyl-1,2,4-triazol-5-yl group and a 3-n-pentyl-4-phenyl-1,2,4-triazol-5-yl group, etc.), a thiadiazolyl group (e.g., a 2-methylthio-1,3,4-thiadiazol-5-yl group and a 2-amino- 1,3,4-thiadiazol-5-yl group, etc.), an oxadiazolyl group (e.g., a 2-phenyl-1,3,4-oxadiazol-5-yl groups etc.), a tetraazaindenyl group (e.g., a 6-methyl-1,3,3a,7-tetraazaindenyl group, 6-n-nonyl-1,3,3a,7-tetraazainden-4-yl group, etc.), an oxazolyl group (e.g., a benzoxazol-2-yl group, etc.) or a thiazolyl group (e.g., a benzothiazol-2-yl group, etc.). Particularly, of P, Q, and R, R can contain a ballast group in its chemical structure and at least one of P, Q, and R represents a Y-S- residue.

The ballast group in the ICC hydroquinone derivatives used in the present invention is an aliphatic group having about 8 to 32 carbon atoms which provides diffusion resistance.

A first characteristic of the hydroquinone derivatives and particularly the compounds represented by the formula (I) is the presence of the Y-S- residue. In general, reducibility, namely DIR-activity of the hydroquinone derivatives, tends to decrease by the introduction of the Z-S- residue. On the contrary, it is possible to increase the reducibility, namely the DIR-activity of the hydroquinone derivatives, by introduction of the Y-S- residue (Y preferably represents an aliphatic residue).

A second characteristic is that is is possible to prevent the so-called "abnormal color development" simultaneously while providing diffusion resistance, if the ballast group and preferably the Y-residue is an aliphatic group having 8 or more carbon atoms. On the other hand, the "abnormal color development" caused by the hydroquinone derivatives is prevented by substitution in the 3- or 4-position.

A third characteristic is that it is possible to increase affinity to organic solvents, couplers, hydroquinone derivatives and ultraviolet light adsorbing agents by introducing the Y-S- residue.

A fourth characteristic is that the hydroquinone derivatives according to the present invention can be easily produced.

These and other characteristics will be understood from the description in this specification.

Examples of compounds of formula (I) are shown in the following

Compound 1
2-n-Dodecylthio-5-(1'-phenyltetrazol-5'-ylthio)hydroquinone

Compound 2
2-n-Octadecylthio-5-(1'-phenyltetrazol-5-ylthio)hydroquinone

Compound 3
2-n-Hexadecylthio-5-(1'-phenyltetrazol-5-ylthio)hydroquinone

Compound 4
2-[2',5'-Dihydroxy-6'-(1''-phenyltetrazol-5''-ylthio)-4'-(1''',1''',3''',3'''-tetramethylbutyl)]phenylthiobenzoic acid Compound 5
2-[2',5'-Dihydroxy-6'-(1''-phenyltetrazol-5''-ylthio)-3'-(1''',1''',3''',3'''-tetramethylbutyl)]phenylthiobenzoic acid Compound 6
2-(1'-Phenyltetrazol-5'-ylthio)-3-phenylthio-6-(1'',1'',3'',3''-tetramethylbutyl)hydroquinone Compound 7
2-(1'-Phenyltetrazol-5'-ylthio)-3-phenylthio-5-(1'',1'',3'',3''-tetramethylbutyl)hydroquinone Compound 8
2,5-Dihydroxy-6-(1'-phenyltetrazol-5'-ylthio)-4-(1'',1'',3'',3''-tetramethylbutyl)phenylthioacetic acid Compound 9
2-[2',5'-Dihydroxy-3'-n-hexadecylthio-6'-(1''-phenyltetrazol-5''-ylthio)]phenylthiobenzoic acid Compound 10
2-n-Hexadecylthio-5-(1'-phenyltetrazol-5'-ylthio)-6-phenylthiohydroquinone Compound 11
4-(1'-Phenyltetrazol-5'-ylthio)-5-hydroxy-7-(1'',1'λ',3'',3''-tetramethylbutyl)benzoxathiol-2-one Compound 12
2-[2',5'-Dihydroxy-6'-(1''-phenyltetrazol-5''-ylthio)-3'-(1''',1''',3''',3'''-tetramethylbutyl)]phenylthiobenzoic acid methyl ester Compound 13
2-[2',5'-Dihydroxy-6'-(1''-phenyltetrazol-5''-ylthio)-4'-(1''',1''',3''',3'''-tetramethylbutyl)]phenylthiobenzoic acid methyl ester Compound 14
2-[2',5'-Dihydroxy-3'-n-pentadecylthio-6'-(1''-phenyltetrazol-5''-ylthio)]phenylthiobenzoic acid methyl ester Compound 15
2-n-Octyloxycarbonylmethylthio-6-phenyl-3-(1'-phenyltetrazol-5'-ylthio)hydroquinone Compound 16
2-p-Nitrophenylthio-3-(1'-phenyltetrazol-5'-ylthio)-6-(1'',1'',3'',3''-tetramethylbutyl)hydroquinone Compound 17
2-(2'-Methylthio-1',3',4'-thiadiazol-5'-ylthio)-6-(1'',1'',3'',3''-tetramethylbutyl)hydroquinone Compound 18
3-(2'-Methylthio-1',3',4'-thiadiazol-5'-ylthio)-6-(1'',1'',3'',3''-tetramethylbutyl)hydroquinone Compound 19

2,3-bis-(2'-Methylthio-1',3',4'-thiadiazol-5-ylthio)-6-(1'',1'',3'',3''-tetramethylbutyl)hydroquinone Compound 20

2-(3'-n-Pentyl-4'-phenyl-1',2,4'-triazol-5'-ylthio)-5-(1',1'',3'',3''-tetramethylbutyl)hydroquinone Compound 21

2-(6'-Methyl-1',3',3a',7'-tetraazainden-4'-ylthio)-6-(1'',1'',3'',3''-tetramethylbutyl)hydroquinone Compound 22

2,3-bis-(6'-Methyl-1',3',3a',7'-tetraazainden-4'-ylthio)-6-(1'',1'',3'',3''-tetramethylbutyl)hydroquinone Compound 23

2-n-Hexadecylthio-5-(2'-methylthio-1',3',4'-thiadiazol-5'-ylthio)hydroquinone

Compound 24

2-[2',5'-Dihydroxy-6'-(2''-methylthio-1'',3'',4''-thiadiazol-5''-ylthio)-3'-(1''',1''',3''',3'''-tetramethylbutyl)]phenylthiobenzoic acid Compound 25

2-(2'-Amino-1',3',4'-thiadiazol-5'-ylthio)-5-(1'',1'λ',3'',3''-tetramethylbutyl)hydroquinone Compound 26

2-[2',5'-Dihydroxy-6'-(2''-amino-1'',3'',4''-thiadiazol-5''-ylthio)-4-(1''',1''',3''',3'''-tetramethylbutyl)]phenylthiobenzoic acid Compound 27

2-(2'-Amino-1',3',4'-thiadiazol-5'-ylthio)-3-n-dodecylthio-6-(1'',1'',3'',3''-tetramethylbutyl)hydroquinone Compound 28

2-(6'-t-Butyl-1,3,3a,7-tetraazainden-4-ylthio)-6-(1'λ',1'',3'',3''-tetramethylbutyl)hydroquinone Compound 29

2-(6-n-Nonyl-1',3',3a',7'-tetraazainden-4'-ylthio)-6-(1'',1'',3'',3''-tetramethylbutyl)hydroquinone Compound 30

2-(4'-Phenyl-1',2',4'-triazol-5'-ylthio)-5-(1'',1'',3'λ',3''-tetramethylbutyl)hydroquinone Compound 31

2-(2'-Phenyl-1',3',4'-oxadiazol-5-ylthio)-5-(1'',1'',3'',3''-tetramethylbutyl)hydroquinone Compound 32

2-(1'-Phenyltetrazol-5'-ylthio)-5-n-octyloxycarbonylmethylthiohydroquinone

Compound 33

2-t-Dodecylthio-5-(1'-phenyltetrazol-5'-ylthio)hydroquinone

Compound 34

2-(Benzoxazol-2'-ylthio)-5-n-octadecylhydroquinone

Compound 35

2-(2'-Methylphenylthio)-6-n-octadecylthio-3-(1'-phenyltetrazol-5''-ylthio)hydroquinone Compound 36

2-n-Octyloxycarbonylmethylthio-3-(1'-phenyltetrazol-5'-ylthio)-6-p-tolylhydroquinone Compound 37

2-Ethoxycarbonylmethylthio-6-n-hexadecylthio-3-(1'-phenyltetrazol-5'-ylthio)hydroquinone Compound 38

2-Phenylthio-3-(1'-phenyltetrazol-5'-ylthio)-5-n-dodecylthiohydroquinone.

The compounds represented by the formula (I) can be synthesized by the method described in U.S. Pat. No. 3,379,529, namely by an addition reaction of a mercapto compound with a benzoquinone.

Examples of a conventional method for the synthesis of the compounds represented by the formula (I) are shown in the following. Unless otherwise indicated, all parts, percents, ratios and the like are by weight.

Synthesis 1 (Compound 3)

316 g of 2-n-hexadecylthio-p-benzoquinone was added to 1 liter of methanol and the mixture was cooled with ice with stirring. A solution prepared by dissolving 155 g of 1-phenyl-5-mercaptotetrazole in 800 ml of methanol was then added dropwise thereto. After the addition, the mixture was cooled with ice with stirring for 3 hours. Then, the mixture was stirred for 8 hours at room temperature (above 20 to 30°C) to precipitate crystals.

The resulting crystals were removed by filtration and recrystallized from benzene. Thus, 350 g of 2-n-hexadecylthio5-(1'-phenyltetrazol-5-ylthio)hydroquinone having a melting point of 129 to 131°C was obtained.

Synthesis 2 (Compound 6)

15 g of 2-(1'-phenyltetrazol-5-ylthio)-6-(1'',1'',3'',-3''tetramethylbutyl)-p-benzoquinone was added to 150 ml of methanol and the mixture was cooled with ice with stirring. To this solution, a solution prepared by dissolving 4.5 g of thiophenol in 25 ml of methanol was added dropwise. After the addition, the mixture was cooled with ice with stirring for 3 hours. The resulting crystals were separated by filtration and recrystallized from a mixture of hexane and ethyl acetate.

Thus, 7.5 g of 2-(1'-phenyltetrazol-5'-ylthio)-3-phenylthio6-(1'',1'',3'',3''-tetramethylbutyl)hydroquinone having a melting point of 147°C was obtained.

Synthesis 3 (Compound 20)

13 g of 3-mercapto-5-n-pentyl-4-phenyl-1,2,4-triazole was dissolved in 200 ml of methanol and the mixture was cooled with ice with stirring. To this solution, 12 g of 2-(1',1',3',3'tetramethylbutyl)-p-benzoquinone was added incrementally. After the addition, the mixture was cooled with ice with stirring for 2 hours and then the mixture was allowed to stand overnight at room temperature. Methanol was removed by condensing under a reduced pressure. Diethyl ether was added to the resulting residue and the resulting crystals were removed. The crystals were recrystallized from ethyl acetate.

5 g of 2-(3-n-pentyl-4'-phenyl-1,2,4-triazol-5'-ylthio)-5-(1'',1'',3'',3''-tetramethylbutyl)-hydroquinone having a melting point of 198°C was obtained.

The adsorbing colloid layer for the organic development inhibitor (ADL) of the present invention means a colloid layer having the ability to adsorb or fix the organic residues which are released from a hydroquinone derivative or formed by development from an organic accelerator to provide an interlayer interimage effect which was previously adsorbed on the silver halide particles in the photosensitive emulsion layer together with the above described hydroquinone derivative to inhibit introduction of the organic residues into the developer, or a colloid layer having the ability to adsorb the development inhibiting residues which are initially released during development to remove them from the developer and the ability to control diffusion of the released development inhibiting residues. Accordingly, it is preferred to position the colloid layer (ADL) of the present invention above or below the photosensitive emulsion layer with respect to the direction of incident light of exposure. This colloid layer contains silver halide particles and can contain a compound having an adsorbing ability such as colloidal silica. Preferably, the silver halide particles have a very fine grain size and contain a very small amount of iodine ion so as to possess a high adsorbing ability. A suitable grain size range for the silver halide grains is about 0.03 microns to 2 microns. Particularly, the silver halide particles preferably have an average grain size of about 0.5 microns or less. Also, preferably the surface of the grains is treated by addition of iodine ions, cyano ions, thiocyanate ions or metal ions such as gold ions or iridium ions, etc., or is etched by addition of a silver halide solvent so that the grains are activated for adsorption. In order to maintain strong adsorption in the developer, preferably the silver halide particles are neither developed nor dissolved in the developer. Accordingly, silver iodobromide particles wherein the particles, which are not chemically ripened, contain less than 10% by mol of silver iodide are preferably used. Particles of silver chlorobromide, silver bromide, silver chlorobromide, or silver iodochloride can also be used.

One characteristic of the present invention is the disposition of the adsorbing colloid layer for the organic development inhibitor (ADL). Firstly the ADL is positioned above the photosensitive emulsion layer containing a hydroquinone derivative of the present invention and the photosensitive emulsion layer for providing an interlayer interimage effect. In this case, the ADL absorbs the development inhibitor released from the photosensitive emulsion layer below and prevents the generation of development mottle by controlling the range affected by the development inhibitor in the planar direction. Secondly, the ADL is positioned below the photosensitive emulsion layer, namely, toward the support side. In this case, the ADL absorbs the development inhibitor released from the above described photosensitive emulsion layer and controls excess spreading of the development inhibitor function in the planar direction, whereby generation of development mottle is prevented. Further, if the ADL is provided on the backside of the support, the ADL absorbs the development inhibitor in the developer to prevent contamination of the developer. In any of the above described first and second embodiments, the silver halide particles in the ADL preferably are fine grains having, more preferably, an average grain size below about 0.2 microns and are composed of silver iodobromide or silver bromide which is difficult to dissolve during the color development. Preferably, the silver halide particles are applied in the amount of 0.01 g to 5 g/m² of the support. It has been found that "development mottle" that is, color mottle in Mackie line-like fine images are caused, if the range in the planar direction of a function of the development inhibitor released by development is too wide. This fact can be improved by providing the ADL according to the present invention.

According to the present invention, not only is the generation of "development mottle" prevented but also uniformity of the developing treatment is remarkably improved consequently. This is because release of the organic development inhibitor in the developer which is a chief cause of contamination of the developer is prevented.

Another characteristic of the present invention is high temperature development. The term "high temperature development" as used in the present invention means development at a high temperature of above about 30°C and preferably about 30 to 40°C or sometimes up to above 60°C. As shown in Japanese Patent Publication 28836/1972 or French Pat. No. 2,132,675, iodine ions released at development are very easily adsorbed by silver chloride or silver bromide of the silver halide particles in the adjacent layer by an exchange reaction and they are, generally, difficult to be released in the developer. Particularly, at high temperature, the exchange reaction is accelerated and the iodine ions are released in the developer with difficulty. The hydroquinone derivatives according to the present invention release organic releasing groups and particularly monothio type development inhibitors in a high concentration corresponding to rapid development in the photosensitive emulsion layer. However, they are easily adsorbed by the silver halide particles used in the ADL. Accordingly, a remarkable effect of the presence of ADL appears at high temperature.

As couplers used in the present invention, 4-equivalent couplers and 2-equivalent couplers are employed with 2-equivalent couplers being preferred. Particularly, couplers represented by the following formulae (II), (III), (IV) and (V) are preferred.

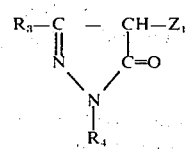

In formula (II), $R_3$ represents an alkyl group selected from primary, secondary and tertiary groups (e.g., methyl, propyl, n-butyl, tert-butyl, hexyl, 2-hydroxyethyl, 2-phenylethyl or pentadecyl, etc.), an aryl group (e.g., phenyl or 2,4-di-tertphenyl, etc.), an alkoxy group (e.g., methoxy, ethoxy, or benzyloxy, etc.), an aryloxy group (e.g., phenoxy, etc.), a heterocyclic group (e.g., quinolinyl, pyridyl, benzofuranyl or oxazolyl, etc.), an amino group (e.g., methylamino, diethylamino, phenylamino, tolylamino, 4-(3-sulfobenzamino)-anilino, 2-chloro-5-acylaminoanilino, 2-chloro-5-alkoxycarbonylanilino or 2-trifluoromethylphenylamino, etc.), an amido group (e.g., alkylcarbamido such as ethylcarbamido, arylcarbamido, heterocyclic carbamido such as benzothiazolylcarbamido, sulfonamido, alkylsulfoamido, arylsulfonamido, or heterocyclic sulfonamido, etc.), or a ureido group (e.g., alkylureido, arylureido or heterocyclic ureido, etc.). The alkyl group or the alkyl moiety of the group for $R_3$ can suitably have 1 to about 20 carbon atoms. $R_4$ represents an aryl group (e.g., naphthyl, phenyl, 2,4,6-trichlorophenyl, 2-chloro-4,6-dimethylphenyl, 2,6-dichloro-4-methoxyphenyl, 4-methylphenyl, 4-acylaminophenyl, 4-alkylaminophenyl, 4-trifluoromethylphenyl or 3,5-dibromophenyl, etc.), a heterocyclic group (e.g., benzofuranyl, benzothiazolyl or quinolinyl, etc.) or an alkyl group (e.g., having 1 to 20 carbon atoms such as methyl, t-butyl or benzyl, etc.). $Z_1$ represents a hydrogen atom or a group which can be released at color development such as a thiocyano group, an acyloxy group, an aryloxy group, an alkoxy group, an alkoxycarbonyl group, an aryloxycarbonyl group, an aryloxycarbonyloxy group, a carboamido group, a sulphonamido group, a di-substituted amino group, an arylazo group or a heterocyclic azo group, etc., which is described in, for example, U.S. Pat. Nos. 3,419,391, 3,252,924, 3,311,476 and 3,227,550 or U.S. Pat. Applications Serial Nos. 461,204, filed Apr. 15, 1974, and 471,639, filed May 20, 1974, etc.

Formula (III)

Formula (III)

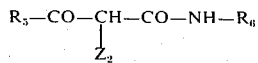

In the formula (III) $R_5$ represents an alkyl group selected from primary, secondary and tertiary alkyl groups (e.g., having 1 to 20 carbon atoms such as tert-butyl, 1,1-dimethylpropyl, 1,1-dimethyl-1-methoxyphenoxymethyl, etc.), or an aryl group (e.g., phenyl, alkylphenyl such as 2-methylphenyl and 3-octadecylphenyl, alkoxyphenyl such as 2-methoxyphenyl and 4-methoxyphenyl, halophenyl, 2-chloro-5-alkylcarbamidophenyl, 2-chloro-5-($\alpha$-(2,4-di-tert-aminophenoxy)butylamido)phenyl, 2-methoxy-5-alkylamidophenyl or 2-chloro-5-sulfoamidophenyl, etc.). $R_6$ represents a phenyl group (e.g., 2-chlorophenyl, 2-halo-5-alkylamidophenyl, 2-chloro-5-($\alpha$-(2,4-di-tert-amylphenoxy)acetamido)phenyl, 2-chloro-5-(4-methylphenylsulfoamido)phenyl or 2-methoxy-5-(2,4-di-tert-amylphenoxy)acetamidophenyl, etc.). $Z_2$ represents a hydrogen atom or a group which can be released at color development such as a halogen atom and particularly a fluorine atom, an acyloxy group, an aryloxy group, a heteroaromatic carbonyloxy group, a sulfimido group, an alkylsulfoxy group, an arylsulfoxy group, phthalimido group, a dioxoimidazolidinyl group, a dioxooxazolidinyl group, a dioxothiazolidinyl group or a dioxomorpholino group, etc., which is described in, for example, U.S. Pat. Nos. 3,227,550, 3,253,924, 3,277,155, 3,265,506, 3,408,194 and 3,415,652, French Pat. No. 1,411,384, British Pat. No. 944,490, 1,040,710 and 1,118,028, German Patent Publications (OLS) No. 2,057,941, 2,163,812, 2,213,461 and 2,219,917, and U.S. Patent Application Ser. No. 469,923, filed May 14, 1974, etc.

Formula (IV)

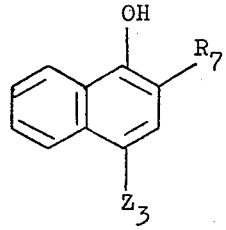

Formula (V)

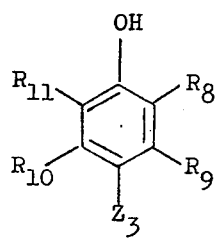

In the formulae (IV) and (V), $R_7$ represents a substituent usually used in cyan couplers, for example, a carbamoyl group (e.g., alkylcarbamoyl, arylcarbamoyl such as phenylcarbamoyl, or heterocyclic carbamoyl such as benzothiazolylcarbamoyl, etc.), a sulfamoyl group (e.g., alkylsulfamoyl, arylsulfamyl such as phenylsulfamoyl or heterocyclic sulfamoyl, et.c), an alkoxycarbonyl group or an aryloxycarbonyl group, etc.; $R_8$ represents an alkyl group, an aryl group, a heterocyclic group, an amino group, a carbamido group (e.g., alkylcarboamido or arylcarboamido, etc.), a sulfonamido group, a sulfamoyl group or a carbamoyl group, etc., and $R_9$, $R_{10}$ and $R_{11}$ each represents the same group defined for $R_8$, and additionally represents a halogen atom or an alkoxy group, etc. The alkyl group and the alkyl moieties of the groups for $R_7$ to $R_{10}$ can suitably contain 1 to 20 carbon atoms. $Z_3$ represents a hydrogen atom or a group which can be released at color development such as a halogen atom, a thiocyano group, a cycloimido group (e.g., maleimido, succinimido or 1,2-dicarboxyimido, etc.), an arylazo group or a heterocyclic azo group, etc.

In order to provide the couplers with diffusion resistance, a hydrophobic residue having about 8 to 32 carbon atoms is introduced into the coupler molecule. Such a residue is called a ballast group. The ballast group can be linked directly to a coupler skeleton or through an imino bond, an ether bond, a carbonamido bond, a sulfonamido bond, a ureido bond, an ester bond, an imido bond, a carbamoyl bond or a sulfamoyl bond, etc.

Examples of ballast groups are shown in the examples of couplers of the present invention given hereinafter and in addition examples of ballast groups are as follows.

I. Alkyl groups and alkenyl groups: e.g., -$CH_2$-$CH(C_2H_5)_2$, -$C_{12}H_{25}$, -$C_{16}H_{33}$, and -$C_{17}H_{33}$ II. Alkoxyalkyl groups: e.g., groups as described in Japanese Patent Publication No. 27563/1964 such as -$(CH_2)_3$-O-$(CH_2)_7CH_3$ and

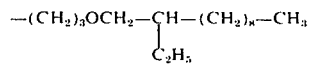

III. Alkylaryl groups:

e.g.,

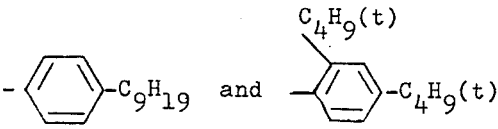

IV. Alkylaryloxyalkyl groups:

e.g.,

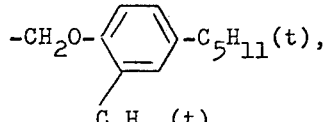

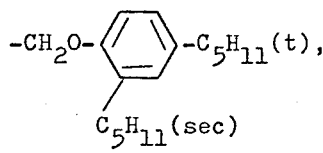

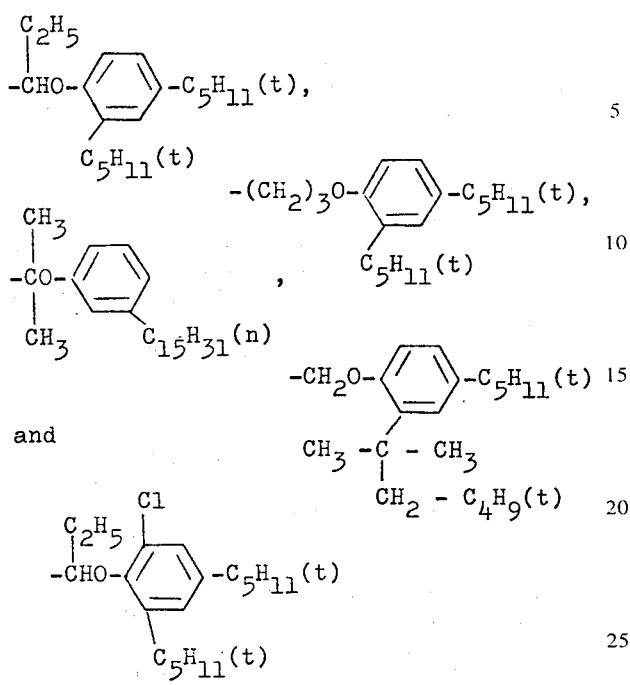

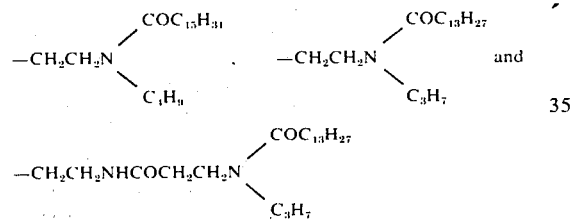

V. Acylamidoalkyl groups:
  e.g., groups as described in U.S. Patent Nos. 3,337,344 and 3,418,129 such as

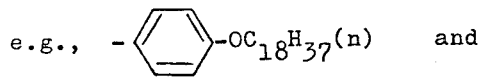

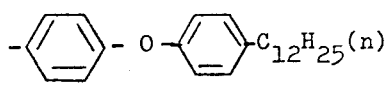

IV. Alkoxyaryl and aryloxyaryl groups:

e.g., $-\langle\bigcirc\rangle-OC_{18}H_{37}(n)$ and $-\langle\bigcirc\rangle-O-\langle\bigcirc\rangle-C_{12}H_{25}(n)$ VII. Residues having a long chain aliphatic group selected from alkyl and alkenyl groups and a water solubilizing group selected from sulfo and carboxy groups:

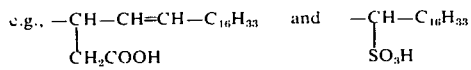

VIII. Alkyl groups substituted with an ester group:

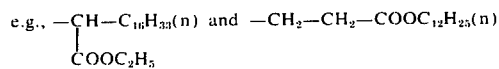

IX. Alkyl groups substituted with an aryl group or a heterocyclic group:

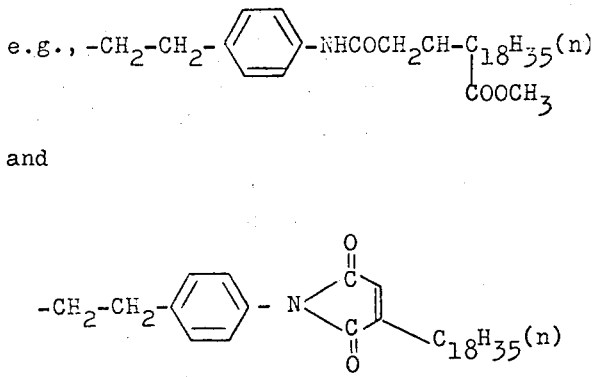

and

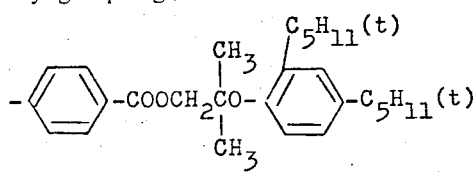

X. Aryl groups substituted with an aryloxyalkoxycarbonyl group: e.g., $-\langle\bigcirc\rangle-COOCH_2\underset{CH_3}{\overset{CH_3}{C}}O-\langle\bigcirc\rangle-C_5H_{11}(t)$ with $C_5H_{11}(t)$ Typical examples of materials which can be used in the present invention are shown in the following. However, the present invention is not to be construed as being limited to these examples.

Yellow Couplers

1. α-{3-[α-(2,4-Di-tert-amylphenoxy)butyramido]-beozoyl}-2-methoxyacetanilide
2. α-Acetoxy-α-3-[γ-(2,4-di-tert-amylphenoxy)-butyramido]-benzoyl-2-methoxyacetanilide
3. N-(4-Anisoylacetamidobenzenesulfonyl)-N-benzyl-N-toluidine
4. α-(2,4-Dioxo-5,5-dimethyl-oxazolidinyl)-α-pivaloyl-2-chloro-5-[α-(2,4-di-tert-amylphenoxy)-butyramido]acetanilide
5. α-(4-Carboxyphenoxy)-α-pivaloyl-2-chloro-5-[α-(2,4-di-tert-amylphenoxy)butyramido]acetanilide
6. α-[3-(1-Benzyl-2,4-dioxo)hydantoinyl]-α-pivaloyl-2-chloro-5-[α-(2,4-di-tert-amylphenoxy)-butyramido]acetanilide
7. α-(4-Methoxybenzoyl)-α-(3,5-dioxomorpholino)-5-[γ-(2,4-di-tert-amylphenoxy)butyramido]-2-chloroacetanilide Magenta Couplers 8. 1-(2,4,6-Trichlorophenyl)-3-(3-(2,4-di-tert-amylphenoxy-acetamido)benzamido)-5-pyrazolone
9. 1-(2,4,6-Trichlorophenyl)-3-{3-[α-(2,4-di-tert-amylphenoxy)-acetamido]benzamido}-4-acetoxy-5-pyrazolone
10. 1-(2,4,6-Trichlorophenyl)-3-tridecylamido-4-(4-hydroxyphenyl)azo-5-pyrazolone
11. 1-(2,4,6-Trichlorophenyl)-3-[(2-chloro-5-tridecanoylamino)anilino]-5-pyrazolone
12. 1-(2,4,6-Trichlorophenyl)-3-(2-chloro-5-tetradecyloxycarbonyl)anilino-4-(1-naphthylazo)-5-pyrazolone
13. 1-(2,4-Di-chloro-6-methoxyphenyl)-3-[(2-chloro-5-tridecanoylamino)anilino]-4-benzyloxycarbonyloxy-5-pyrazolone
14. 1-(2,4,6-Trichlorophenyl)-3-{3-[(2,4-di-tert-amylphenoxy)acetamido]-benzamido}-4-piperidino-5-pyrazolone 15. 1-(2,4,6-Trichlorophenyl)-3-{2-chloro-5-[α-(2,4-di-tert-amylphenoxy)-butyramido]anilino}-4-N-phthalimido-5-pyrazolone 16. 1-(2,4,6-Trichlorophenyl)-3-(2-chloro-5-tetradecylaminoanilino-4-(3-methyl-4-hydroxyphenylazo)-5-pyrazolone

Cyan Couplers 17. 1-Hydroxy-N-[γ-(2,4-di-tert-amylphenoxypropyl)]-2-naphthamide 18. 1-Hydroxy-4-[2-(2-hexyldecyloxycarbonyl)-phenylazo]-2-[N-(1-naphthyl)]naphthamide 19. 1-Hydroxy-4-chloro-N-[α-(2,4-di-tert-amylphenoxy)butyl]-2-naphthamide 20. 5-Methyl-4,6-dichloro-2-[α-(3-n-pentadecylphenoxy)-butylamino]-phenol 21. 1-Hydroxy-4-(2-ethyloxycarbonylphenylazo)-N-(2-ethylamyl)-2-naphthamide The hydroquinone derviatives used in the present invention can be used together with the so-called "DIR couplers", "ICC couplers" or organic accelerators having an interlayer interimage effect. For example, there are couplers represented by the following formula (VI).

Formula (VI)

Cp - $Z_4$

In the formula (VI), Cp presents a coupler residue which reacts by coupling with the oxidation product of aromatic primary amine color developing agents and $Z_4$ represents an organic residue which is released on coupling with the oxidation product of the aromatic primary amine color developing agent and has a property of inhibiting the development by diffusing after the release. The Cp residue can be chosen from the residues of 4-equivalent couplers used in color photographic materials. Examples of such couplers include 5-pyrazolone couplers, cyanoacetylcoumarone couplers, imidazolone couplers, acylacetanilide couplers, pivaloylacetanilide couplers, aroylacetamide couplers, naphthol couplers and phenol couplers. Examples of $Z_4$ include a heterocyclic residue having a 1-triazole ring or 1-diazole ring as described in U.S. Patent Application Ser. No. 454,525, filed Mar. 25, 1974, and residues described in Japanese Patent Publication 8750/1972, U.S. Pat. No. 3,617,291, 3,622,328, 3,632,373, 3,620,745, 3,620,747 and 3,615,506 and British Pat. No. 1,201,110, 1,261,061, 1,269,075 and 1,269,073.

Hydroquinone derivatives used in the present invention are organic accelerators having an interlayer interimage effect, for example, such as those described in U.S. Patent Application Ser. No. 484,742, filed July 8, 1974, U.S. Pat. No. 3,536,487, U.S. Defensive Publications T 909,022 and T 909,023 and German Patent Publications (OLS) 2,043,943 and 2,043,944, etc.

22. α-Benzoyl-α-(2-benzothiazolylthio)-4-[N-(γ-phenylpropyl)-N-(4-tolyl)sulfamoyl]acetanilide 23. 1,14-[γ-(2,4-di-tert-amylphenoxybutyramido)-phenyl]-3-piperidinyl-4-(1-phenyl-5-tetrazolylthio)-5-pyrazolone 24. 1-(2,4,6-Trichlorophenyl)-3-{4-[α-(2,4-di-tert-amyl-phenoxy)butyramido]anilino}-4-(1-phenyl-5-tetrazolylthio)-5-pyrazolone 25. 1-{4-[α-(2,4-Di-tert-amylphenoxy)acetamido]-phenyl}-3-methyl-4-(5- or 6-bromo-1-benzotriazolyl)-5-pyrazolone 26. 5-Methoxy-2-[α-(3-n-pentadecylphenoxy)-butyramido]-4-(1-phenyl-5-tetrazolylthio)phenol 27. N-[α-(2,4-Di-tert-amylphenoxy)acetyl]ω-(1-phenyl-5-tetrazolylthio)-m-aminoacetophenone 28. α-Pivaloyla-α-(5-or 6-bromo-1-benzotriazolyl)-5-[α-(2,4-di-tert-amylphenoxy)propionamido]-2-chloroacetanilide 29. α-(4-Methoxybenzoyl)-α-(5- or 6-nitro-1-benzotriazolyl)-5-[γ-(2,4-di-t-amylphenoxy)-butylamido]-2-chloroacetanilide 30. α-(4-Stearyloxybenzoyl)-α-(5- or 6-bromo-1-benzotriazolyl)-2-methoxyacetanilide 31. 1-Hydroxy-4-(1-phenyltetrazolylthio)-N-[(2-chloro-5-hexadecyloxy)phenyl]-2-naphthamide.

Typical examples of the organic accelerators having an interlayer interimage effect which can be used in the present invention are shown in the following. The invention is not to be construed as being limited to these examples.

32. 5-(3-Ethyl-2-benzothiazolylidene)-3-benzylrhodanine 33. 5-[3-(γ-Sulfopropyl)-2-benzoxazolylidene]-3-cyclohexyl-rhodanine 34. 5-(3-Methyl-2-benzoselenazolylidene)-3-(γ-sulfobutyl)-rhodanine 35. 5-{3-(β-Hydroxyethyl)-β-naphthoxazolylidene]-1-phenyl-2-thiohydantoin 36. 2-Thioxo-3-ethylbenzothiazole 37. 2-Mercapto-5-methylbenzothiazole 38. 2-Thioxo-3-n-propylbenzoxazole 39. 1,3-Di-n-propyl-2-thioxobenzimidazole 40. N-Methyl-2-thioxo-6-chloroquinoline.

The hydroquinone derivatives used in the present invention can be incorporated by adding couplers to an emulsion or by preparing an emulsion of a coupler and adding the emulsion to a silver halide emulsion. For example, a method which comprises dissolving the coupler in an organic solvent having a high boiling point, e.g., a phosphate ester or a phthalate ester such as tricresyl phosphate or dibutyl phthalate, a fatty oil which is liquid at room temperature (about 20° to 30°C) such as acetyltri-(2-ethylhexylcitrate or tributylglycerol, waxes, higher aliphatic acids and esters thereof, N-n-butylacetanilide or N,N-diethylcapramide, and dispersing the solution in a hydrophilic colloid solution can be employed. For example, the emulsified dispersion can be produced by the method described in U.S. Pat. Nos. 2,304,939, 2,322,027, 2,801,170, 2,801,171, 2,949,360 and 1,143,707. Further, the method described in U.S. Pat. No. 3,379,529 can be used to incorporate the hydroquinone derivative.

The couplers used in the present invention can be added as an emulsified dispersion using the above described conventional method. Conventionally used anionic surface active agents (e.g., sodium alkylbenzene sulfonate, sodium dioctylsulfosuccinate, sodium dodecylsulfate, sodium alkylnaphthalene sulfonate and Fischer type couplers, etc.), amphoteric surface active agents (e.g., N-tetradecyl-N,N-di-polyethylene-α-betaine, etc.) and nonionic surface active agents (e.g., sorbitan monolaurate, etc.) can be used as dispersion assistants.

The couplers are generally used in the amount of about 1/100 times to 2 times on a molar basis to the moles of silver halide. The interlayer color correction couplers can be used alone or as a mixture with other couplers, and they are used in the amount below about 50% by mol and preferably below 20% by mol based on the total amount of couplers in the photographic material of the present invention. The hydroquinone derivatives of the present invention can be used alone or as a mixture with couplers according to the purpose, and suitably in an amount below about 50% mol and preferably below 10% by mol based on the total amount of couplers in the photographic material of the present invention.

The organic accelerators having an interlayer interimage effect are added after being dissolved in a water miscible organic solvent such as methanol, ethanol, pyridine, methyl cellosolve or acetone or in water. Usually, they are employed in an amount about $10^{-7}$ to $10^{-3}$ mol per mol of silver halide.

The silver halide emulsions which can be used for the photosensitive emulsion layers in the present invention are dispersions wherein silver chloride, silver bromide or a mixed silver halide such as silver chlorobromide, silver iodobromide or silver chloroiodobromide is finely dispersed in a hydrophilic high molecular weight material such as gelatin. The dispersion can be chosen from those having a uniform grain size to those having a wide distribution of particle size and those dispersions having an average grain size of about 0.1 microns to about 3 microns are suitable depending on the purpose of use of the photosensitive material. These silver halide emulsions can be prepared by mixing, for example, using a single- or double-jet method or a control double-jet method, and by ripening, for example, by an ammonia method, a neutral method or an acid method, etc.

The silver halide emulsions used in the photosensitive emulsion layers in the invention can be chemically ripened using conventional chemical sensitization methods. For example, the gold sensitization method described in U.S. Pat. Nos. 2,399,083, 2,597,856 and 2,597,915, the reduction sensitization method described in U.S. Pat. Nos. 2,487,850 and 2,521,925, the sulfur sensitization method described in U.S. Pat. Nos. 1,623,499 and 2,410,689, the method for sensitizing using metal ions other than silver described in U.S. Pat. Nos. 2,448,060, 2,566,245 and 2,566,263, or combinations of these sensitization methods can be employed.

Spectral sensitization methods conventionally used for silver halide photosensitive materials can also be employed. For example, the emulsion can be spectrally sensitized with cyanine or merocyanine dyes as described in U.S. Pat. Nos. 2,519,001, 2,666,761, 2,734,900, 2,739,964, 3,481,742, etc. In addition, conventionally used stabilizers, e.g., 4-hydroxy-1,3,3a,7-tetrazaindene derivatives, etc., antifogging agents, e.g., mercapto compounds or benzotriazole derivatives, coating asistants, hardening agents, wetting agents and sensitizing agents, e.g., onium derivatives such as the quaternary ammonium salts described in U.S. Pat. Nos. 2,271,623, 2,288,226 and 2,334,864 or polyalkylene oxide derivatives as described in U.S. Pat. Nos. 2,708,162, 2,531,832, 2,533,990, 3,210,191 and 3,158,484 can be employed. Furthermore, anti-irradiation dyes can be added, and a filter layer, a mordant dye layer or a colored layer containing a hydrophobic dye can be included as a layer of the color photographic material of the present invention.

The photosensitive emulsions used in the present invention can be applied to many kinds of supports. For example, a cellulose acetate film, a polyethylene terephthalate film, a polyethylene film, a polypropylene film, a glass plate, barita paper, a resin laminated paper and synthetic paper can be suitably used. A suitable coating amount of the silver halide ranges from about 0.01 g to 20 g (as silver)/m², preferably 0.1 g to 10 g (as silver)/m².

The color photographic sensitive materials according to the invention are treated with a color developer containing p-phenylenediamine derivatives or p-aminophenol derivatives as a color developing agent. Examples of preferred p-phenylenediamines include p-amino-N-ethyl-N-β-(methanesulfonamidoethyl)-m-toluidinesesquisulfate monohydrate, diethylamino-p-phenylenediamine sesquisulfate, p-amino-N,N-diethyl-m-toluidine hydrocloride and p-amino-N-ethyl-N-β-hydroxyethylaniline sesquisulfate monohydrate, etc. Further, known developers for color negative photographic materials, cinema color negative or positive photographic materials, color papers or instant color photographic materials can be used. For example, the color developing processings described substantially in Japanese Patent Publication 35749/1970, Japanese Patent Applications 67798/1969, 13313/1971 and 19516/1971, H. Gordon, The British Journal of Photography, page 558 et seq., Nov. 15, 1954; ibid, page 440, et seq., Sept. 9, 1955, and ibid, page 2 et seq., Jan. 1, 1956; S. Horwitz, ibid, page 212 et seq., Apr. 22, 1960; E. Gehret, ibid, page 122 et seq., Mar. 4, 1960, and ibid, page 396 et seq., May 7, 1965; J. Meech, ibid., page 182, et seq., Apr. 3, 1959; and German Patent Publication (OLS) No. 2,238,051 can be used.

The black-white photographic sensitive materials of the present invention can be developed using a black-white developing agent such as a hydroquinone, a p-aminophenol derivative or a 1-phenyl-3-pyrazolidone derivative. For example, the developing processing described in C. E. K. Mees and T. H. James, The Theory of the Photographic Process 3rd Edition Chapters 13 and 14 (1966).

Examples are described in the following to illustrate the invention in greater detail, although the present invention is not to be construed as being limited to these examples. Unless otherwise indicated, all parts, percents, ratios and the like are by weight.

EXAMPLE 1

Sample A was produced by applying in turn a first layer, a second layer, a third layer, a fourth layer and a fifth layer to a transparent cellulose triacetate film support as shown in FIG. 1 with the first, second, third, fourth and fifth layers corresponding to the reference numerals 1 to 5 in FIG. 1, respectively. The composition and the preparation of the coating solutions used for each layer were as follows.

First Layer (BL):

To 1 kg of a silver iodobromide emulsion (silver content: 0.52 mol, iodine content: 6% by mol), 600 g of Emulsion I which was prepared by emulsifying a solution of 100 g of Coupler (4) in 100 ml of dibutylphthalate and 200 ml of ethyl acetate in 1 kg of a 10% gelatin aqueous solution using 4 g of sodium dodecylbenzene sulfonate was added. The mixture was applied to form the first layer. The silver content of the first layer was 0.6 g/m².

Second Layer (GL):

1 kg of a silver iodobromide emulsion (silver content: 0.6 mol, iodine content: 6% by mol) was spectrally sensitized using $2 \times 10^{-4}$ mols of Sensitizing Dye I and $6 \times 10^{-5}$ mols of Sensitizing Dye II. To this emulsion, 600 g of Emulsion II which was produced by emulsifying a solution containing 100 g of Coupler (8) and 5 g of Compound (10) in 100 ml of tricresyl phosphate and 200 ml of ethyl acetate in 1 kg of a 10% gelatin aqueous solution was added. The silver content of the second layer was 1.0 g/m².

Third Layer (ADL):

1 kg of a fine grain silver iodobromide emulsion (silver content: 0.5 mol, iodine content: 2% by mol, average particle size: 0.05 $\mu$) was applied to provide a dry thickness of 3 $\mu$ (silver content: 21 g/m²).

Fourth Layer (RL):

1 kg of a silver iodobromide emulsion (same as the first layer) was spectrally sensitized with $4 \times 10^{-5}$ mols of sensitizing Dye III and $1 \times 10^{-5}$ mols of Sensitizing Dye IV. To this emulsion, 450 g of Emulsion III which was produced using 100 g of Coupler (17) in the same manner as in Emulsion II was added. The silver content of the fourth layer was 1.7 g/m².

Fifth Layer (PL):

Gelatin Protective Layer.
A gelatin layer in a dry thickness of 0.7 $\mu$.

To each coating solution, sodium polyvinylbenzene sulfonate as a viscosity increasing agent, sodium dodecylbenzene sulfonate as a surface active agent and a gelatin hardening agent, 2-hydroxy-4,6-dichlorotriazine, were added. The materials used for producing Sample A were as follows:

Sensitizing Dye I: Anhydro-9'-ethyl-5,5'-dichloro-3,3'-disulfopropyloxacarbocyanine sodium salt.

Sensitizing Dye II: Anhydro-5,6,5',6'-tetrachloro-1,1'-diethyl-3,3'-disulfopropoxyethoxyethylimidazolocarbocyanine hydroxide sodium salt.

Sensitizing Dye III: Anhydro-5,5'-dichloro-3,3'-disulfopropyl-9-ethylthiacarbocyanine hydroxide pyridinium salt.

Sensitizing Dye IV: Anhydro-9-ethyl-3,3'-di-(3-sulfopropyl)-4,5,4',5'-dibenzothiacarbocyanine hydroxide triethylamine salt.

Sample B was produced in the same manner as Sample A but the third layer was a gelatin layer having the same thickness which did not contain a silver halide emulsion.

After stepwise exposing Sample A and Sample B to light from a green light source, they were exposed uniformly to light from a red light source. Then, they were subjected to development processing at 38°C using the following steps (1).

| 1. | Color Development | 3 minutes and 15 seconds |
|---|---|---|
| 2. | Bleaching | 6 minutes and 30 seconds |
| 3. | Water Wash | 3 minutes and 15 seconds |
| 4. | Fixation | 6 minutes and 30 seconds |
| 5. | Water Wash | 3 minutes and 15 seconds |
| 6. | Stabilization | 3 minutes and 15 seconds |

The compositions of the processing solutions used in each step were as follows.

| Color Developer | | |
|---|---|---|
| Sodium Nitrilotriacetate | 1.0 | g |
| Sodium Sulfite | 4.0 | g |
| Sodium Carbonate | 30.0 | g |
| Potassium Bromide | 1.4 | g |
| Hydroxylamine Sulfate | 2.4 | g |
| 4-(N-Ethyl-N-β-hydroxyethylamino)-2-methyl-aniline Sulfate | 4.5 | g |
| Water to make | 1 | liter |
| Bleaching Solution | | |
| Ammonium Bromide | 160.0 | g |
| Aqueous Ammonia Solution (28%) | 25.0 | ml |
| Iron Ethylenediamine Tetraacetic Acid Sodium Salt | 130 | g |
| Glacial Acetic Acid | 14 | ml |
| Water to make | 1 | liter |
| Fixing Solution | | |
| Sodium Tetrapolyphosphate | 2.0 | g |
| Sodium Sulfite | 2.0 | g |
| Ammonium Thiosulfate (70%) | 175.0 | ml |
| Sodium Thiosulfite | 4.6 | g |
| Water to make | 1 | liter |
| Stabilizing Solution | | |
| Formalin (40%) | 8.0 | ml |
| Water to make | 1 | liter |

Figure 4:
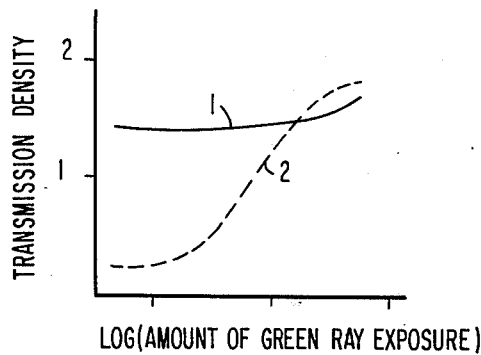
FIGS. 4, 5, 6 and 7 show characteristics curves obtained in the Examples.
Figure 5:
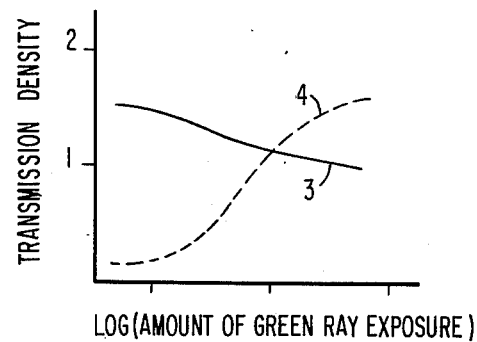

The red light transmission densities (Curves 1 and 3) and the green light transmission densities (Curves 2 and 4) of the processed Samples A and B were determined for comparison. The results of the determination on Sample A are shown in FIG. 4 and those on Sample B are shown in FIG. 5. In Sample B, the green density increases as the exposure increases, while the red density decreases. On the contrary, in Sample A having the ADL of the present invention, although the green density is the same as that of Sample B, no decrease in the red density was observed. It can be understood from these results that a mercapto compound formed by color development from Compound 10 in the second layer in Sample B is diffused into the fourth layer to inhibit the development of the fourth layer, while the mercapto compound is absorbed by the third layer (ADL) in Sample A and diffusion into the fourth layer was substantially inhibited, and thus the purpose of the present invention has been attained by the third layer.

On the other hand, Samples A and B were exposed to light uniformly under the same conditions as described above from a red light source and then they were subjected to line exposure of 500 microns width by 10 millimeter length from a green light source. They were then developed by the following Conditions $a$, $b$, and $c$.

| Condition a | at 24°C for 15 minutes |
|---|---|
| Condition b | at 30°C for 7 minutes |
| Condition c | at 38°C for 4 minutes |

In Sample B, violet - magenta development mottle appeared around the blue image when Sample B was developed under Condition $b$ or $c$. However, no development mottle appeared in Sample A under any condition.

EXAMPLE 2

(Demonstration of the effect of ADL)

Figure 2:
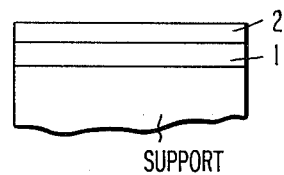

Sample C was produced by applying a first layer and a second layer to a transparent cellulose triacetate support as shown in FIG. 2 with the layers shown below corresponding to the reference numerals in FIG. 2. The composition of each layer was as follows.

First Layer (RL):

The same as the fourth layer of Samples A and B.

Second Layer (ADL):

1 kg of a fine grain silver iodobromide emulsion (silver content: 0.6 mol, iodine content: 14% by mol, average particle size: 0.03 $\mu$) was applied so as to provide a dry thickness of 3 $\mu$ (applied silver content: 2.3 g/m$^2$).

Sample D was produced in the same manner as Sample C but the second layer was a gelatin layer without the silver halide but having the same thickness.

Samples C and D were exposed stepwise to light and subjected to developing processing (2) in the same manner as in Example 1 but 0.019 g of 1-phenyl-5-mercaptotetrazole was added to 1 liter of the color developing solution in the developing processing (1) of Example 1.

Figure 6:
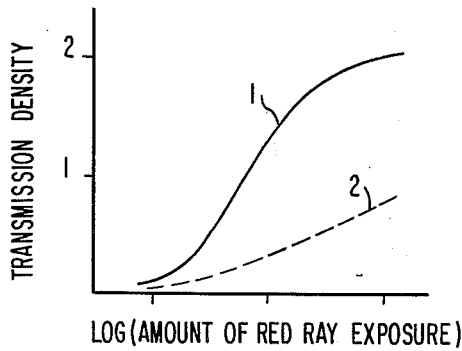
Figure 7:
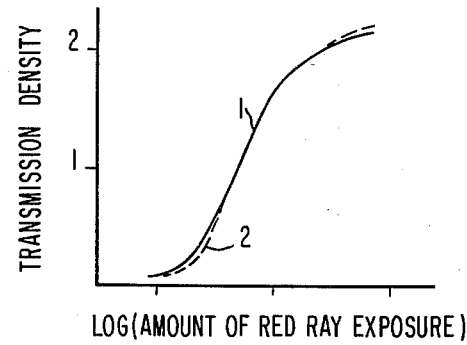

The red densities of Sample C at developing processing (1) and (2) are shown in FIG. 7 and those of Sample D are shown in FIG. 6. In Sample D, developing processing (2) caused a remarkable decrease in the density as compared with the developing processing (1). However, in Sample C, a difference in densities was not observed between the developing processing (1) and (2). It can be understood from those results that 1-phenyl-5-mercaptotetrazole diffuses into the first layer in Sample D in developing processing (2) to inhibit the development, while the 1-phenyl-5-mercaptotetrazole is absorbed by the second layer (ADL) in Sample C in developing processing (2) and the diffusion into the first layer is substantially prevented, and thus the purpose of the present invention can be attained by the second layer. Namely, it can be understood that a sample having ADL can be normally developed even if a developer which is contaminated by a released development inhibitor is used.

EXAMPLE 3

Figure 3:
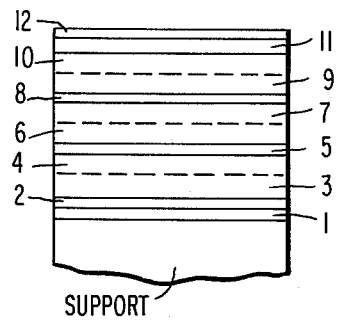

Multilayer photographic material E comprising layers having the following compositions on a cellulose triacetate support was produced as shown in FIG. 3 with the layers listed below corresponding to the reference numerals in FIG. 3.

First Layer: Antihalation Layer (AHL)
  A gelatin layer containing black colloidal silver.
Second Layer: Middle Layer (ML)
  A gelatin layer containing emulsified dispersion of 2-n-dodecylthiohydroquinone.
Third Layer: First Red Sensitive Emulsion Layer (RL$_1$)
  Silver iodobromide emulsion (iodine: 8% by mol) applied silver content: 1.2 g/m$^2$
  Sensitizing Dye I (as described in Example 1) 6 × 10$^{-5}$ mol per mol of silver
  Sensitizing Dye II (as described in Example 1) 1.5 × 10$^{-5}$ mol per mol of silver
  Coupler (17) 0.09 mol per mol of silver
  Coupler (18) 0.02 mol per mol of silver
Fourth Layer: Second Red Sensitive Emulsion Layer (RL$_2$)
  Silver iodobromide emulsion (iodine: 8% by mol), applied silver content: 1.1 g/m$^2$

| | |
|---|---|
| Sensitizing Dye I | 3 × 10$^{-5}$ mol per mol of silver |
| Sensitizing Dye II | 1.2 × 10$^{-5}$ mol per mol of silver |
| Compound I | 0.02 mol per mol of silver |
| Coupler (18) | 0.06 mol per mol of silver |
| Coupler (17) | 0.01 mol per mol of silver |

Fifth Layer: Middle Layer (ML)
  The same as the second layer.

Sixth Layer: First Green Sensitive Emulsion Layer (GL$_1$)
  Silver iodobromide emulsion (iodine: 8% by mol), applied silver content: 1.4 g/m$^2$
  Sensitizing Dye III (as described in Example 1): 3 × 10$^{-5}$ mol per mol of silver
  Sensitizing dye IV (as described in Example 1): 1 × 10$^{-5}$ mol per mol of silver
  Coupler (13) 0.05 mol per mol of silver
  Coupler (10) 0.003 mol per mol of silver
Seventh Layer: Second Green Sensitive Emulsion Layer (GL$_2$)
  Silver iodobromide emulsion (iodine: 6% by mol), applied silver content: 1.5 g/m$^2$

| | |
|---|---|
| Sensitizing Dye III | 2.5 × 10$^{-5}$ mol per mol of silver |
| Sensitizing Dye IV | 0.8 × 10$^{-5}$ mol per mol of silver |
| Coupler (8) | 0.02 mols per mol of silver |
| Coupler (16) | 0.02 mols per mol of silver |
| Coupler (31) | 0.0003 mols per mol of silver |

Eighth Layer: (YFL)
  A gelatin layer containing an emulsified dispersion of yellow colloidal silver and 2-n-dodecylthio-hydroquinone in an aqueous gelatin solution.
Ninth Layer: First Blue Sensitive Emulsion Layer (BL$_1$)
  Silver iodobromide emulsion (iodine: 6% by mol), applied silver content 1 g/m$^2$
  Coupler (4) 0.25 mol per mol of silver
  Compound 1 0.01 mol per mol of silver Tenth Layer:
    Second Blue Sensitive Emulsion Layer (BL$_2$)
  Silver iodobromide emulsion (iodine: 6% by mol) applied silver content 1.1 g/m$^2$
  Coupler (4) 0.06 mol per mol of silver
  Compound 1 0.002 mol per mol of silver
Elventh Layer: ADL
  The same as the second layer of Sample C in Example 2
Twelfth Layer: Protective Layer (PL)
  A gelatin layer containing polymethyl methacrylate particles having a particle size of about 1.5 $\mu$.

A gelatin hardening agent (2-hydroxy-4,6-dichlorotriazine), a surface active agent (sodium dodecylbenzene sulfonate) and a viscosity increasing agent (sodium polyvinylbenzene sulfonate) were added to each layer.

Sample F was produced in the same manner as Sample E but the Eleventh layer of Sample E was a gelatin layer which did not contain silver halide.

Samples E and F were cut in a width of 35 mm and exposed uniformly to white light. They were then processed in the processing (1). In Sample F, the red density, the green density and the blue density notably decreased as the amount processed increased. On the contrary, in Sample E having the ADL of the present invention, the densities decreases were very small. Accordingly, it can be understood that the purpose of the present invention was attained.

EXAMPLE 4

Sample G was produced by applying an ADL containing silver bromide particles having an average particle size of 0.15 microns to the back of the cellulose triacetate film support of Sample F in Example 3 so as to provide an applied silver content of 5.5 g/m$^2$. It was cut in a width of 35 mm, exposed uniformly to white light and processed by processing (1) as in Example 3. Although the color densities decreased as increase in the treated amount, the degree of decrease thereof in Sample G was less than that of Sample F.

EXAMPLE 5

Sample H was produced by applying in turn an ADL, BL, GL, RL and PL to a cellulose triacetate film support using the same coating solutions as described for Sample A of Example 1. After being exposed uniformly to light from a red light source, the sample was exposed linewise to light from a green light source. Development mottle in Sample H caused by the development at the above described Condition (c) were remarkably less than that of Sample B.

EXAMPLE 6

In Example 2, Organic Accelerator (37) or (36) having an interlayer interimage effect was added to the developer in an amount of $1 \times 10^{-4}$ mol per liter of the developer, and Samples C and D were developed in the same manner as described in Example 2. In Sample C having the ADL, the color densities hardly decreased. On the contrary, in Sample D, the color densities decreased and progress of the development was inhibited.

This means that there is no disadvantage at development if photosensitive materials having the ADL of the invention are used, even if the developer is contaminated with organic accelerators.

EXAMPLE 7

Sample K was produced by applying the following first layer and second layer to a polyethylene terephthalate film support.

First Layer: Silver Iodochlorobromide Emulsion Layer

To a silver iodochlorobromide emulsion (bromide content: 17% by mol, iodide content: 0.7% by mol, silver content 0.52 mol/kg of the emulsion), a dispersion of Compound 37 in N-n-butylacetanilide was added in an amount of 0.025 mol per mol of silver halide. The mixture was then applied (applied silver content: 1.5 kg/m²).

Second Layer: ADL

The third layer of Example 1 was applied so as to provide a dry thickness of 2 μ.

Sample K was exposed to light from X-ray edge linear exposure, developed at 30°C for 4 minutes and fixed. Thus, an excellent edge effect was obtained and the image sharpness increased without development mottle being caused.

| Developer Composition | | |
|---|---|---|
| Water | 500 | ml |
| Hydroquinone | 6 | g |
| Sodium Bisulfite | 38 | g |
| N-Methyl-p-aminophenol Sulfate | 0.3 | g |
| Sodium Carbonate (anhydrous) | 19 | g |
| Potassium Bromide | 0.9 | g |
| Sodium Metabisulfite | 1.5 | g |
| Tartaric Acid | 0.7 | g |
| Water to make | 1 | liter |

The present invention can be widely applied in producing photographic recording materials containing a hydroquinone derivative which releases a photographically active compound such as a development inhibitor or a development accelerator at development. Particularly, the present invention can be applied to color photographic materials having good color reproduction, color negative photographic materials, color positive transparent photographic materials, color papers, color reversal photographic materials, instant photographic materials and direct positive type photographic materials, etc. Furthermore, it is particularly useful for black-white- or color photographic materials wherein uniform development is required and contamination of the developer causes difficulty, and photographic materials for industry such as color X-ray photographic materials, plate making photographic materials and microfilm photographic materials, etc.

While the invention has been described in detail and with reference to specific embodiments thereof, it will be apparent to one skilled in the art that various changes and modifications can be made therein without departing from the spirit and scope thereof.

What is claimed is:

1. A photographic photosensitive material comprising a support having thereon a silver halide photosensitive emulsion layer containing a hydroquinone derivative which releases a development inhibitor at development and including on said emulsion layer or between said emulsion layer and said support an adsorbing colloid layer containing silver halide particles which are not substantially developed by development for adsorbing said development inhibitor.

2. The photographic photosensitive material of claim 1, wherein said hydroquinone derivative has the General Formula (I)

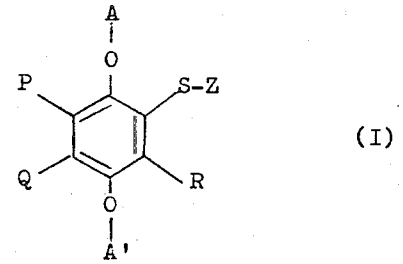

wherein A and A' each represents a hydrogen atom or a group which is released by alkali, and wherein A' may form a ring together with R or Q; P, Q and R each represents a hydrogen atom, an alkyl group, an aryl group, an -S-Y residue, a hydroxyl group, a halogen atom, an -S-Z residue, an alkoxy group, an aryloxy group, or a heterocyclic ring; Y represents an alkyl group or an aryl group; and Z represents a heterocyclic residue which is substantially photographically inert in a bonded state.

3. The photographic photosensitive material of claim 2, wherein Z represents a tetrazolyl group, a triazoyl group, a thiadiazolyl group, an oxadiazolyl group, a tetraazaindenyl group, an oxazoyl group, or a thiazolyl group.

4. The photographic photosensitive material of claim 1, wherein said hydroquinone derivative contains a ballast group having about 8 to 32 carbon atoms.

5. The photographic photosensitive material of claim 1, wherein the silver halide particles of the silver halide emulsion have an average grain size below 0.5 microns.

6. The photographic photosensitive material of claim 5, wherein the grain size is below 0.2 microns.

7. The photographic photosensitive material of claim 1, wherein the silver halide particles in the adsorbing colloid layer are present in an amount of about 0.01 to 5 g/m² of the support.

8. The photographic photosensitive material of claim 1, wherein said adsorbing colloid layer is adjacent said silver halide emulsion layer containing said hydroquinone derivative and is positioned above said silver halide emulsion layer in the direction of incident light of exposure.

9. The photographic photosensitive material of claim 1, wherein said adsorbing colloid layer is adjacent said silver halide emulsion layer containing said hydroquinone derivative and is below said silver halide emulsion layer in the direction of incident light upon exposure.

10. The photographic photosensitive material of claim 1, wherein said adsorbing colloid layer includes additionally colloidal silica.

11. The photographic photosensitive material of claim 1, wherein said silver halide emulsion layer contains at least one coupler represented by the following formula (II)

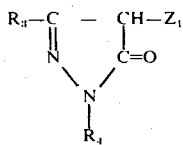 (II)

wherein $R_3$ represents an alkyl group, an aryl group, an alkoxy group, an aryloxy group, a heterocyclic group, an amino group, an amido group, or an ureido group; $R_4$ represents an alkyl group or an aryl group; $Z_1$ represents a hydrogen atom or a group capable of being released at color development; of the General Formula (III)

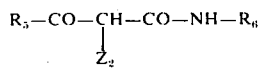 (III)

wherein $R_5$ represents an alkyl group or an aryl group; $R_6$ represents a phenyl group; and $Z_2$ represents a hydrogen atom or a group capable of being released at color development; or a compound of the General Formula (IV)

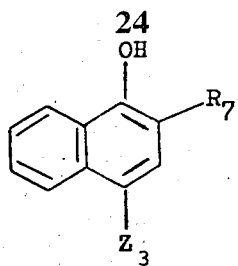 (IV)

or the General Formula (V)

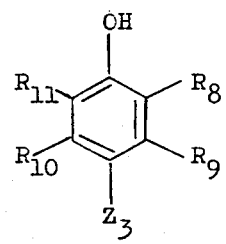 (V)

wherein $R_7$ represents a carbamyl group, a sulfamyl group, an alkoxycarbamyl group or an aryloxycarbamyl group;

$R_8$ represents an alkyl group, an aryl group, a heterocyclic group, an amino group, a carbamido group, a sulfamido, a sulfamyl group or a carbamyl group; $R_9$, $R_{10}$ and $R_{11}$ each represents the same group as defined for $R_8$ and additionally represents a halogen atom or an alkoxy group; and $Z_3$ represents a hydrogen atom or a group capable of being released at color development.

12. A process for producing a image free of development mottle comprising processing an exposed photographic photosensitive material of claim 1 to processing at a temperature above 30°C.

13. The photographic photosensitive material of claim 2, wherein at least one of P, Q and R represents the -S-Y residue.

* * * * *